US011038445B2

(12) United States Patent
Ye et al.

(10) Patent No.: US 11,038,445 B2
(45) Date of Patent: Jun. 15, 2021

(54) DUAL-SENSING FEEDBACK AND TRANSMISSION SYSTEM FOR LINEAR MOTOR

(71) Applicant: Tsinghua University, Beijing (CN)

(72) Inventors: Peiqing Ye, Beijing (CN); Luhong Zhang, Beijing (CN); Hui Zhang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 50 days.

(21) Appl. No.: 16/607,271

(22) PCT Filed: Dec. 4, 2017

(86) PCT No.: PCT/CN2017/114462
§ 371 (c)(1),
(2) Date: Oct. 22, 2019

(87) PCT Pub. No.: WO2019/100440
PCT Pub. Date: May 31, 2019

(65) Prior Publication Data
US 2020/0304045 A1    Sep. 24, 2020

(30) Foreign Application Priority Data
Nov. 22, 2017  (CN) .......................... 201711173108.0

(51) Int. Cl.
*H02P 6/16* (2016.01)
*H02P 25/064* (2016.01)
*H02P 6/00* (2016.01)

(52) U.S. Cl.
CPC ................ *H02P 6/16* (2013.01); *H02P 6/006* (2013.01); *H02P 25/064* (2016.02); *H02P 2203/05* (2013.01)

(58) Field of Classification Search
CPC ........................................................ H02P 6/16
USPC .................................................... 318/135, 34
See application file for complete search history.

(56) References Cited

U.S. PATENT DOCUMENTS 5,982,124 A * 11/1999 Wang ................... G05B 13/024
                                                              318/286
7,548,037 B2 *  6/2009 Boisvert ................ B60J 7/0573
                                                              318/466

OTHER PUBLICATIONS

WIPO, ISR for PCT/CN2017/114462, dated Aug. 3, 2018.

* cited by examiner

*Primary Examiner* — David Luo
(74) *Attorney, Agent, or Firm* — Hodgson Russ LLP

(57) ABSTRACT

Disclosed is a dual-sensing feedback and transmission system for a linear motor. The system includes a linear motor, a transmission mechanism, and a dual-sensing displacement detection mechanism. One end of the transmission mechanism is fixedly connected to a mover of the linear motor, and the other end thereof is located outside a stator of the linear motor and fixedly connected to a leaf of a multi-leaf collimator directly or by means of a connecting block. The dual-sensing displacement detection mechanism is a dual-sensing linear displacement sensor, and includes two sets of reading devices for reading displacement information, and a matching reference ruler. The reading devices are fixed to an end or exterior of a casing of the stator of the linear motor close to the leaf of the multi-leaf collimator. The reference ruler is fixed onto a connecting rod.

4 Claims, 1 Drawing Sheet

DUAL-SENSING FEEDBACK AND TRANSMISSION SYSTEM FOR LINEAR MOTOR

CROSS-REFERENCE TO RELATED APPLICATIONS

This application is based on and claims priority to a U.S. national phase application of International Application No. PCT/CN2017/114462, filed on Dec. 4, 2017, which claims priority to Chinese Patent Application Serial No. 201711173108.0, filed on Nov. 22, 2017, the entire disclosures of which are incorporated by reference herein.

FIELD

The present disclosure relates to a technical field of medical equipment and motors, and more particularly to a dual-sensing feedback and transmission system for a linear motor used to drive a leaf of a multi-leaf collimator in radiotherapy equipment.

BACKGROUND

Multi-leaf collimators are important mechanical components in linear acceleration collimation systems of modern medical radiotherapy equipment, and mainly used for conformation and intensity modulation of cancer target areas. The multi-leaf collimator includes numerous lead-tungsten alloy leaf, and the multi-leaf collimator is connected with a rotating rack. Each leaf is connected to a corresponding motor driving mechanism, a transmission mechanism, a displacement detecting mechanism, and a control system, so as to be moved independently. Each leaf is moved to a corresponding position based on a position command sent by the control system. The numerous leaf constitute a shape in equal proportion to a cancer cell tissue to realize conformation with the target area.

In the prior patents, rotary motors and screw nut pairs are typically used to constitute motor driving mechanisms of leaf. However, due to the presence of speed-reduction and commutation mechanisms of screw nut pairs, the above method cannot provide high movement velocity and will reduce movement accuracy and positioning accuracy, failing to satisfy conformal and intensity-modulated requirements, and consequently prolonging the patient treatment time.

In addition, for radiotherapy equipment as Class III medical instruments, in order to ensure safety and reliability during treatment process, the displacement detecting mechanism of the multi-leaf collimator needs to have a redundant design, that is, a double-insurance or dual-sensing design. The displacement detecting mechanism of the existing multi-leaf collimator adopts a rotary encoder or a Hall sensor. The rotary encoder is mainly used for position feedback of the rotary motor and is not suitable for a linear motor, and the Hall sensor for displacement detection of the linear motor has poor accuracy. Meanwhile, an array of tungsten alloy leaf of the multi-leaf collimator together with its motor driving mechanism, transmission mechanism and displacement detecting mechanism, is installed in a small space, resulting in a large limitation on volume. The existing designs have a large overall structure, leading to an increased size of the rotating rack for connecting the multi-leaf collimator, which is also disadvantageous to the development of miniaturization of modern radiotherapy equipment.

SUMMARY

In order to solve the above problems in the related art, the present disclosure provides a dual-sensing feedback and transmission system for a linear motor used to drive a leaf of a multi-leaf collimator in radiotherapy equipment.

The present disclosure adopts the following technical solutions.

A dual-sensing feedback and transmission system for a linear motor includes: a linear motor comprising a stator and a mover axially movable along the stator; a transmission mechanism configured as a connecting rod, the connecting rod having a first end fixedly connected to a first end of the mover, and a second end located outside the stator and fixedly connected to a leaf of a multi-leaf collimator directly or by means of a connecting block; and a dual-sensing displacement detecting mechanism configured as a dual-sensing linear displacement sensor, and comprising two sets of reading devices for reading displacement information and a matching reference ruler, in which the two sets of reading devices are fixed to an end or exterior of a casing of the stator of the linear motor close to the leaf of the multi-leaf collimator, electrical parts of the two sets of reading devices are connected to a drive control system of the linear motor, and the reference ruler is fixed to the connecting rod, wherein the dual-sensing displacement detecting mechanism is used to detect linear displacement of the leaf of the multi-leaf collimator and transmit displacement information to the drive control system of the linear motor.

The technical effect achieved by the present disclosure is that the displacement feedback detection using two sets of reading devices for reading displacement information can meet the dual-sensing requirements of Class III medical instruments, ensuring safety and reliability in the treatment process, and detecting the movement position of the leaf accurately to ensure the movement accuracy and positioning accuracy of the leaf; the design of fixing the matching reference ruler on the connecting rod can shorten the length of the whole system, and realize the integration of the structural functions of mechanical transmission and position detection; the design of arranging the dual-reading device on the stator or outside the stator can reduce the size of the system and meet the size requirements for the multi-leaf collimator in narrow installation spaces.

BRIEF DESCRIPTION OF THE DRAWINGS

These and/or other aspects and advantages of embodiments of the present disclosure will become apparent and more readily appreciated from the following descriptions made with reference the accompanying drawings, in which.

REFERENCE NUMERALS

1: leaf of multi-leaf collimator, 2: transition block, 3: connecting rod, 4: optical grating ruler, 5: dual-reading head; 6: stator of linear motor, 7: mover of linear motor.

DETAILED DESCRIPTION

The present disclosure will be described in detail with reference to the accompanying drawings, in order to understand the present disclosure more profoundly, and appreciate purposes, embodiments and advantages of the present disclosure more clearly. It should be understood that a specific embodiment described herein is one of implementations of the present disclosure, and is intended to illustrate the present disclosure rather than limit the present disclosure.

Figure 1:
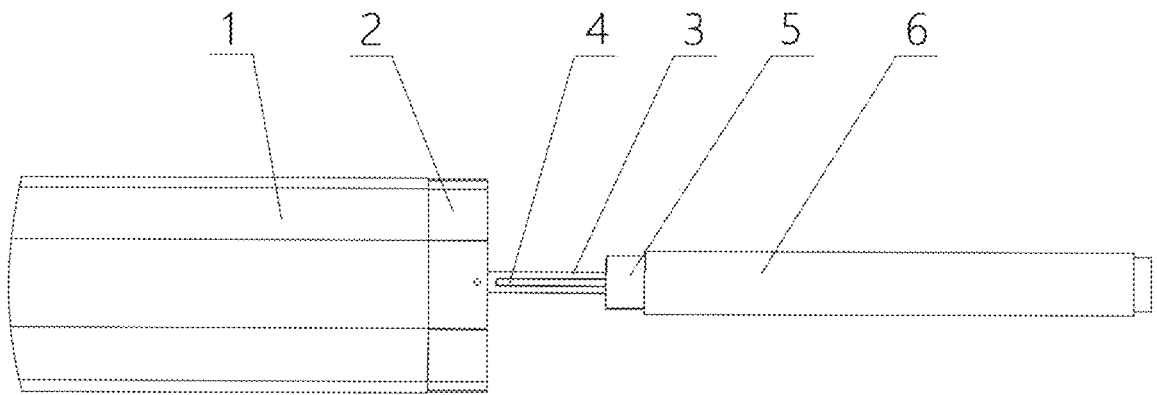
FIG. 1 is a front view of one embodiment of the present disclosure.
Figure 2:
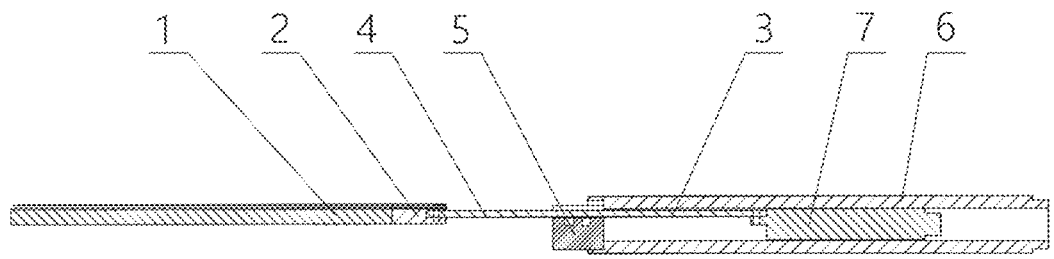
FIG. 2 is a sectional view of FIG. 1.
Figure 3:
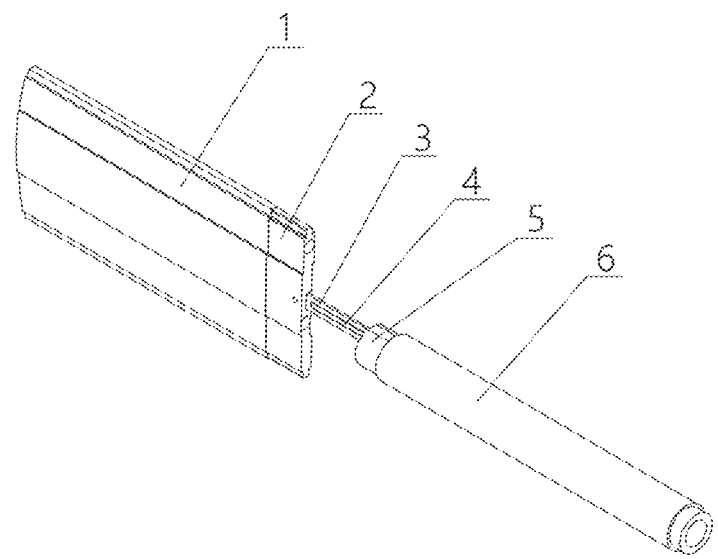
FIG. 3 is an isometric view of one embodiment of the present disclosure.

FIGS. 1 to 3 are a front view, a sectional view, and an isometric view of one embodiment of the present disclosure respectively, and the specific structure of this embodiment will be described below in conjunction with the several views.

A dual-sensing feedback and transmission system based on a linear motor according to the embodiment of the present disclosure is used to drive a leaf of a multi-leaf collimator in radiotherapy equipment and feed position information about the leaf of the multi-leaf collimator. This system includes: a linear motor including a stator 6 and a mover 7 axially movable along the stator 6; a transmission mechanism configured as a connecting rod 3, the connecting rod having a first end fixedly connected to a first end of the mover 7, and a second end located outside the stator 6 and fixedly connected to the leaf 1 of the multi-leaf collimator directly or by means of a connecting block 2; and a dual-sensing displacement detecting mechanism configured as a dual-sensing linear displacement sensor, and including two sets of reading devices 5 for reading displacement information and a matching reference ruler 4, in which the two sets of reading devices 5 are fixed to an end or exterior of a casing of the stator 6 of the linear motor close to the leaf 1 of the multi-leaf collimator, and electrical parts of the reading devices are connected to a drive control system of the linear motor, and the reference ruler 4 is fixed to the connecting rod 3; the dual-sensing displacement detecting mechanism is used to detect linear displacement of the leaf 1 of the multi-leaf collimator and transmit such information to the drive control system of the linear motor.

Specific implementations and functions of various components of the present disclosure are elaborated as follows.

The linear motor adopts a permanent magnet synchronous motor, a linear direct current (DC) motor, a linear induction motor, a linear reluctance motor, a linear piezoelectric motor, and etc. The shape of the linear motor is cylindrical, flat, U-shaped, square or the like. The linear motor of the present embodiment employs a cylindrical permanent magnet synchronous linear motor, and a coil inside the stator 6 of the linear motor is connected to the drive control system. Further, a length of the mover 7 of the linear motor of the present embodiment is smaller than a length of the stator 6, so that the present system is further reduced in terms of its size along an axis of the linear motor, to meet installation size requirements for multi-motor arrays of the multi-leaf collimator in narrow space.

One implementation of the dual-sensing displacement detecting mechanism uses a dual-sensing optical grating sensor under a transmissive or reflective detection principle. The two sets of reading devices for reading displacement information employ a dual-reading head 5 fixed to the end or exterior of the casing of the stator 6 of the linear motor close to the leaf of the multi-leaf collimator. The matching reference ruler adopts an optical grating ruler 4 fixed to the connecting rod 3 (the fixing method can include sticking the reference ruler onto the connecting rod or directly engraving reference scale of the reference ruler on the connecting rod). The dual-reading head 5 is a sensor having two sets of reading functions, which can simultaneously detect two pieces of displacement information of the same leaf of the multi-leaf collimator, and transmit the information to the drive control system of the linear motor, thereby satisfying position detection and redundant design requirements for double insurance in medical equipment, and considerably reducing the spatial size of the structure. The optical grating ruler 4 is made of glass or steel strip materials, and the optical grating pitch is customized according to the required detection accuracy, such as a resolution of 0.1 μm, 0.5 μm, 1 μm, 5 μm, 10 μm, and 20 μm. The reading head of the present embodiment has a cylindrical shape fitted with the casing structure of the stator of the linear motor, and is fixed to the end of the casing of the linear motor stator close to the leaf 1 of the multi-leaf collimator, thereby shortening the overall size, with the diameter being 16.8 mm and the length being 16 mm. The optical grating ruler of the present embodiment is of a rectangular parallelepiped shape and is disposed along a length of the connecting rod, and has a length of 90 mm, a width of 3 mm, and a height of 0.1 mm.

Another implementation of the dual-sensing displacement detecting mechanism uses a dual-sensing magnetic grating sensor. The two sets of reading devices for reading displacement information employ a dual magnetic head, and the matching reference ruler adopts a magnetic ruler. The dual magnetic head adopts two sets of magnetic pickup devices, and is fixed to the end or exterior of the casing of the stator 6 of the linear motor close to the leaf 1 of the multi-leaf collimator. The magnetic ruler is fixed to the connecting rod 3 (the fixing method can include adhesion or recording magnetic signals into the connecting rod of magnetically non-conductive material). The shape of the dual magnetic head is square or cylindrical, and the magnetic ruler has a long strip shape with a resolution of 1 μm to 5 μm. The dual magnetic head can simultaneously detect two pieces of displacement information of the same leaf of the multi-leaf collimator, and transmit the information to the drive control system of the linear motor, thereby satisfying position detection and redundant design requirements for double insurance in medical equipment. The fixation of the magnetic ruler to the connecting rod 3 can reduce the spatial size of the overall invention.

The connecting rod 3 acts as the transmission mechanism and fixed together with the reference ruler 4 to perform a position detection effect. When the dual-reading head or the dual magnetic head of the dual-sensing displacement detecting mechanism is fixed to the end of the casing of the linear motor stator, considering the installation of the dual-reading head or the dual magnetic head, the connecting rod is disposed off-axis with respect to an axis of the casing of the linear motor stator. When the dual-reading head or the dual magnetic head of the dual-sensing displacement detecting mechanism is fixed to the exterior of the casing of the linear motor stator, the connecting rod can be located at the axis of the casing of the linear motor stator. The connecting rod of the present embodiment is made of stainless steel (other metal materials can also be used; when the reference ruler adopts the magnetic ruler, the connecting rod is made of magnetically non-conductive material), and has a size of 107 mm*6 mm*2 mm. The optical grating ruler 4 is fixed to the connecting rod by adhesion or slotting the connecting rod.

The connecting block 2 is used to enhance stability of the connection between the connecting rod 3 and the leaf 1 of the multi-leaf collimator. The connecting block of the present embodiment is provided with bolt holes, so as to be connected with the connecting rod 3 and the leaf 1 of the multi-leaf collimator. In addition, the connection between the connecting block with the connecting rod and the leaf of the multi-leaf collimator can be achieved by welding or riveting.

The working process of the embodiment of the present disclosure is as follows: after the linear motor receives a drive control signal of the control system, the coil of the stator 6 of the linear motor is energized and generates a magnetic field, and interacts with the mover 7 of the linear motor to produce thrust, which is transmitted to the connecting rod 3 and the connecting block 2, thereby pushing the leaf 1 of the multi-leaf collimator to move. Meanwhile, since the reference ruler is fixed to the connecting rod 3, the dual-reading device can capture the linear displacement generated during the movement of the connecting rod 3, which is equivalent to the position information of the leaf, and then feed the position information to the control system, thereby forming position closed-loop control. At the same time, the dual-sensing design, that is, the redundant design, can meet the dual-sensing requirements in radiotherapy.

What is claimed is:

1. A dual-sensing feedback and transmission system for a linear motor, comprising:
    a linear motor comprising a stator and a mover axially movable along the stator;
    a transmission mechanism configured as a connecting rod, the connecting rod having a first end fixedly connected to a first end of the mover, and a second end located outside the stator and fixedly connected to a leaf of a multi-leaf collimator directly or by means of a connecting block; and
    a dual-sensing displacement detecting mechanism configured as a dual-sensing linear displacement sensor, and comprising two sets of reading devices for reading displacement information and a matching reference ruler, wherein the two sets of reading devices are fixed to an end or exterior of a casing of the stator of the linear motor close to the leaf of the multi-leaf collimator, electrical parts of the two sets of reading devices are connected to a drive control system of the linear motor, and the reference ruler is fixed to the connecting rod; the dual-sensing displacement detecting mechanism is used to detect linear displacement of the leaf of the multi-leaf collimator and transmit displacement information to the drive control system of the linear motor.

2. The dual-sensing feedback and transmission system according to claim 1, wherein the two sets of reading devices for reading displacement information employ a dual-reading head, and the matching reference ruler adopts an optical grating ruler, wherein the dual-reading head is a sensor having two sets of reading functions, and configured to simultaneously detect two pieces of displacement information of the same leaf of the multi-leaf collimator and transmit the information to the drive control system of the linear motor.

3. The dual-sensing feedback and transmission system according to claim 1, wherein the two sets of reading devices for reading displacement information employ a dual magnetic head, and the matching reference ruler adopts a magnetic ruler, wherein the dual magnetic head adopts two sets of magnetic pickup devices and is configured to simultaneously detect two pieces of displacement information of the same leaf of the multi-leaf collimator and transmit the information to the drive control system of the linear motor.

4. The dual-sensing feedback and transmission system according to claim 1, wherein the linear motor is any one selected from a permanent magnet synchronous motor, a linear direct current motor, a linear induction motor, a linear reluctance motor, and a linear piezoelectric motor.

* * * * *